United States Patent [19]

Klueppel et al.

[11] Patent Number: 4,726,943

[45] Date of Patent: Feb. 23, 1988

[54] ANTI-CARIES COMPOSITION

[75] Inventors: Hans-Juergen Klueppel, Duesseldorf; Walter Ploeger, Hilden; Hinrich Moeller, Monheim, all of Fed. Rep. of Germany

[73] Assignee: Henkel Kommanditgesellschaft auf Aktien, Duesseldorf, Fed. Rep. of Germany

[21] Appl. No.: 791,257

[22] Filed: Oct. 25, 1985

[30] Foreign Application Priority Data

Oct. 25, 1984 [DE] Fed. Rep. of Germany ....... 3439094

[51] Int. Cl.$^4$ ............................ A61K 7/22; A61K 7/16
[52] U.S. Cl. ......................................... 424/54; 424/57; 424/49
[58] Field of Search ............................... 424/49, 57, 54

[56] References Cited

U.S. PATENT DOCUMENTS

| 3,488,419 | 1/1970 | McCune et al. | 424/49 |
| 3,502,587 | 3/1970 | Stanford et al. | 252/189 |
| 3,925,456 | 12/1975 | Ploger et al. | 260/502.5 |
| 3,941,772 | 3/1976 | Ploger et al. | 260/239 |
| 3,984,543 | 10/1976 | Ploger et al. | 424/204 |
| 3,988,443 | 10/1976 | Ploger et al. | 424/200 |
| 4,311,662 | 1/1982 | Bellos | 422/12 |

FOREIGN PATENT DOCUMENTS 003560M 4/1965 France .
1394172 5/1975 United Kingdom .

OTHER PUBLICATIONS

Calc. Tiss. Res. 11: 10–22 (1973).
Caries Res. 11: 9–15 (1977).
OTC Review on Dentifrices and Dental Care Agents, vol. 080248 of the Proprietory Association.

*Primary Examiner*—J. R. Brown
*Assistant Examiner*—F. T. Moezie
*Attorney, Agent, or Firm*—Ernest G. Szoke; Henry E. Millson, Jr.; Mark A. Greenfield

[57] ABSTRACT

Oral and dental preparations containing as an active ingredient an anti-caries effective amount of a $C_{2-4}$ alkoxylated trihydric to hexahydric $C_{3-12}$ aliphatic polyol wherein at least one hydroxyl moiety is esterified with phosphoric acid, or a physiologically compatible water soluble salt thereof.

30 Claims, No Drawings

ANTI-CARIES COMPOSITION

BACKGROUND OF THE INVENTION

1. Field of the Invention

This invention relates to oral and dental hygienic preparations effective against caries through the presence of water-soluble salts of phosphoric acid esters of alkoxylated polyols. The salts reduce the solubility and inhibit the crystal growth and phosphate ion exchange of hydroxyl apatite (main component of tooth enamel and dental calculus).

2. Statement of the Related Art

Oral and dental hygiene preparations are products used to clean and care for the teeth, the oral cavity and the throat. In addition to eliminating halitosis and removing coatings, the function of oral and dental hygiene preparations is to prevent dental diseases, such as caries and periodontosis, and also the formation of dental calculus (tartar).

It is known that water-soluble organic phosphates have a caries-prophylactic effect. Additives which have been proposed for oral and dental hygiene preparations include, for example, mono- and disodium glycerophosphate, fructose-6-phosphate, sorbitol-6-phosphate, glucose-1-phosphate and glucose-6-phosphate. Salts of phosphoric acid esters of lactose and sucrose have also been described as cariostatic components. Although these products are effective to a certain extent in reducing the solubility of apatite and in inhibiting crystal growth, the level of their effectiveness is not sufficient for adequate protection against the demineralization of dental enamel.

U.S. Pat. No. 3,488,419 discloses oral compositions for calculus retardation which are organic polyphosphonates containing at least two geminal or three vicinal phosphono moieties.

U.S. Pat. No. 4,311,662, which relates to corrosion inhibitors for highly oxygenated systems such as used in oil, gas, and earth drilling, describes a process for the esterification of alkoxylated polyols with phosphoric acid.

DESCRIPTION OF THE INVENTION

It has been found that phosphoric acid esters of alkoxylated trihydric to hexahydric aliphatic polyols or physiologically compatible water-soluble salts thereof are considerably more effective than the corresponding non-alkoxylated polyol phosphates in reducing the solubility and in inhibiting the crystal growth of hydroxyl apatite and the exchange of phosphate ions between hydroxyl apatite and the solution. Accordingly, these products are suitable for use as caries inhibitors in oral and dental hygiene preparations.

The present invention therefore affords oral and dental hygiene preparations having an improved effect against caries which contain as their active component at least one phosphoric acid ester of at least one alkoxylated trihydric to hexahydric, $C_{3-12}$ aliphatic polyol, which has been obtained by addition of from 1 to 15 mols of at least one $C_{2-4}$ alkylene oxide onto the polyol and esterification of at least one and preferably all of the free hydroxyl groups of the alkoxylate with phosphoric acid, or at least one physiologically compatible, water-soluble salt thereof.

The phosphoric acid esters of the alkoxylated polyols are known or may be obtained by known methods. Suitable polyols include at least one of glycerol, erythritol, trimethylol propane, pentaerythritol, arabitol, xylitol, sorbitol, mannitol, diglycerol, triglycerol, dipentaerythritol or trimethylol ethane. The addition of $C_{2-4}$ alkylene oxides, i.e. ethylene oxide, propylene oxide or butylene oxide, preferably ethylene oxide or butylene oxide or both, onto the polyols is carried out by methods known from the literature, including using basic catalysts such as NaOH, KOH, sodium methylate, calcium acetate, or using acidic catalysts such as boron trifluoride, antimony pentachloride, triethyloxonium fluoroborate or $SnCl_4$. It is preferred to use phosphoric acid esters of adducts of from 1 to 10 mols of ethylene oxide and/or propylene oxide with glycerol, erythritol, trimethylol propane or pentaerythritol. The phosphoric acid esters of adducts of from 1 to 7 mols of ethylene oxide with glycerol are particularly effective in inhibiting the crystal growth of hydroxyl apatite, and are most preferred.

Esterification of the alkoxylated polyols with phosphoric acid may be carried out, for example, by the process described in above-mentioned U.S. Pat. No. 4,311,662. In this case, it is best to use a ratio of from 0.5 to 1.0 mol of $P_2O_5$ perhydroxyl equivalent of the alkoxylate. Products are obtained of which 40 to 100% of the hydroxyl groups have been converted into the phosphoric acid ester group. Although products in which at least one of the free hydroxyl groups is esterified with phosphoric acid are effective, a high degree of phosphating, i.e. preferably the esterification of substantially all free hydroxyl groups of the alkoxylate, has proved to be particularly effective. In addition to the organic phosphoric acid esters, the products primarily contain orthophosphates as secondary product inorganic phosphates, which does not detract from the cariostatic effect and, accordingly, may remain in the product. The degree of phosphating may be calculated from the analytical data for the inorganic phosphate content and the total phosphate content.

After esterification, the phosphoric acid esters of the alkoxylated polyols are neutralized with inorganic or organic bases and are thus converted into physiologically compatible, water-soluble salts. Suitable salts are the alkali salts, for example sodium and/or potassium salts, the ammonium salts, mono-, di- and triethanolammonium salts, the calcium or magnesium salts. Other bases suitable for salt formation include guanidine, aminoacid esters, for example the $C_{12-18}$ fatty alcohol esters of lysine, fatty alkyl-$(C_{12-18})$-alkoxyalkylamines, 2-hydroxyalkyl-$(C_{12-18})$-amines and adducts thereof with ethylene oxide. The sodium and potassium salts of the phosphoric acid esters are preferably used.

The oral and dental hygiene preparations according to the invention may be presented in any of the various forms normally used for products of this type, for example mouthwashes, toothpastes, tooth gels, tooth powders, topical solutions and pastes, pastilles, and chewing gum. The preparation should contain a caries-inhibitive amount, preferably from 0.05 to 5.0% by weight of the phosphoric acid esters. To obtain a significant caries-inhibiting effect, however, contents of from 0.1 to 2% by weight are generally sufficient in toothpastes, tooth powders and tooth gels. In mouthwashes intended for use in undiluted form, adequate effects can be obtained with concentrations of from 0.05 to 1.0% by weight, whereas in mouthwash concentrates which are diluted before use, adequate effects can be obtained with higher concentrations resulting in the prescribed use ratio upon dilution.

In chewing gum, oral pastilles, solutions, pastes, and ointments, which may have to be applied several times a day and are inevitably swallowed, however, the dosage should not exceed 1% by weight of the preparation.

In addition to the phosphoric acid esters, the oral and dental hygiene preparations according to the invention may contain all those additives and carriers normally used for the particular formulation. For mouthwashes, the oral and dental hygiene preparations according to the invention may be combined with at least one of aqueous-alcoholic solutions differing in strength of ether-oils, emulsifiers, astringent and toning drug extracts, auxiliary caries-inhibiting additives, antibacterial additives and flavor correctants. At least one surface active substance, for example anionic, nonionic, zwitterionic and ampholytic surfactants, may also be added in the usual quantities.

Toothpastes or tooth creams are generally understood to be gel-like or paste-like preparations of at least one of water, thickeners, humectants, abrasives or polishes, surfactants, sweeteners, flavor correctants, flavorings, deodorizing agents and also agents active against oral and dental diseases. Any one or combination of the usual polishes, such as chalk, dicalcium phosphate, insoluble sodium metaphosphate, aluminium silicates, calcium pyrophosphate, finely particulate synthetic resins, silicas, aluminium oxide and aluminium oxide trihydrate, may be used in the toothpastes according to the invention.

Particularly suitable polishes for the toothpastes according to the invention comprise completely or predominantly finely particulate xerogel silica, hydrogel silica, precipitated silica, aluminium oxide trihydrate and finely particulate α-aluminium oxide, or mixtures of these polishes, used in quantities of from 15 to 40% by weight of the toothpaste. The humectants used are, primarily, low molecular weight polyethylene glycols, glycerol, sorbitol or mixtures thereof in quantities of up to about 50% by weight. Among the known thickeners, finely particulate gel silicas and nonionic hydrocolloids, such as carboxymethyl cellulose, hydroxyethyl cellulose, hydroxypropyl guar, hydroxyethyl starch, polyvinyl pyrrolidone, high molecular weight polyethylene glycol, vegetable gums, such as tragacanth, agaragar, carrageen moss, gum arabic, xanthan gum and carboxyvinyl polymers, or their mixtures, are suitable.

Surfactants useful in the oral and dental hygiene preparations according to the invention are preferably anionic high-foam surfactants, such as: linear sodium $C_{12-18}$-alkyl sulfates; sodium salts of $C_{12-16}$ linear alkyl polyglycol ether sulfates containing from 2 to 6 glycol ether groups in the molecule; alkyl-($C_{12-16}$)-benzene sulfonates; linear alkane-($C_{12-18}$)-sulfonates; sulfosuccinic acid mono-alkyl-($C_{12-18}$)-esters; sulfated fatty acid monoglycerides; sulfated fatty acid alkanolamides; sulfoacetic acid alkyl-($C_{12-18}$)-esters; and acyl sarcosides, acyl taurides and acyl isothionates all containing from 8 to 18 carbon atoms in the acyl moiety. Nonionic surfactants, such as ethoxylates of fatty acid mono- and diglycerides, fatty acid sorbitan esters and ethylene oxide-propylene oxide block polymers, are also suitable.

Other standard toothpaste additives useful in this invention are:

preservatives and antimicrobial agents: such as p-hydroxybenzoic acid methyl, ethyl or propyl ester, sodium sorbate, sodium benzoate, bromochlorophene, phenyl salicylic acid esters, thymol, their mixtures, and the like;

anti-calculus agents, such as organophosphates, for example 1-hydroxyethane-1,1-diphosphonic acid, 1-phosphonopropane-1,2,3-tricarboxylic acid and others, including those known from U.S. Pat. Nos. 3,488,419, 3,941,772 and 3,988,443 (and corresponding Canadian Pat. No. 1,029,020 and published German application No. 23 43 196); U.S. Pat. Nos. 3,925,456 and 3,984,543 (and corresponding Canadian Pat. No. 1,017,356 and published German application No. 23 43 195); and published U.K. application No. 1,394,172 (and corresponding published German application No. 22 24 430); and their mixtures;

other caries inhibitors such as: sodium fluoride, sodium monofluorophosphate, tin fluoride and their mixtures;

sweeteners such as: sodium saccharin, aspartame, sucrose, lactose, maltose, fructose;

flavorings such as: peppermint oil, spearmint oil, eucalyptus oil, aniseed oil, fennel oil, caraway oil, methyl acetate, cinnamic aldehyde, anethole, vanillin, thymol and mixtures of these and other natural and synthetic flavorings;

pigments such as titanium dioxide;

dyes which are physiologically compatible;

buffers such as: primary, secondary or tertiary alkali phosphates or citric acid/sodium citrate; and wound-healing and inflammation-inhibiting substances, such as: allantoin, urea, azulene, camomile active substances and acetyl salicylic acid derivatives, and their mixtures.

By virtue of the presence of this invention's phosphoric acid esters of alkoxylated polyols, the dental and oral hygiene preparations according to the invention not only have a caries-inhibiting effect, but they also successfully counteract the formation of calculus. The production of the phosphoric acid esters in the form of the sodium salts is described in the following Examples which also demonstrate their effectiveness in reducing the solubility of hydroxyl apatite (ASR), inhibiting the crystal growth of hydroxyl apatite (CGI) and inhibiting the exchange of phosphate ions in hydroxyl apatite (PIE). Examples of the typical oral and dental hygiene preparations according to the invention are also described.

EXAMPLES

1. Production of the phosphoric acid ester Na salts,

The phosphoric acid ester-Na-salts listed in the following Table were produced by the following general procedure:

1.1 Alkoxylation

The addition of ethylene oxide (E.O.) or propylene oxide (P.O.) onto the glycerol was carried out in known manner by reaction in a pressure vessel in the presence of catalytically active quantities of sodium methylate at a temperature of from 150° to 175° C. The products were characterized by the hydroxyl equivalent weight which was calculated from the hydroxyl number (OH No.)

$$\left[ Val_{(OH)} = \frac{56110}{\text{OH No.}} \right]$$

1.2 Phosphating

One hydroxyl equivalent of the alkoxylate according to 1.1 was slowly added with stirring at 40° to 50° C. to 169 g (1 mol of $P_2O_5$) of polyphosphoric acid ($P_2O_5$ content 84% by weight). On completion of the addition, the temperature was slowly increased to 95°–100° C. and left at that level while stirring for 3 hours. Thereafter 350 ml of water were added to the reaction mixture which was then heated for 30 minutes to boiling point. The brown-colored solution was then treated with 10 g of active carbon, filtered, cooled and adjusted to pH 7 by the addition of 50% sodium hydroxide. The solutions were used for the following measurements without isolation of the phosphoric acid ester-Na-salts. The active substance content of the solutions was determined by determining the water content (% of active substance = 100 − % $H_2O$).

2. Determining the reduction in apatite solubility (ASR)

2.1 Blank test 0.5 g of hydroxyl apatite powder (specific surface 60 $m^2/g$, Merck) was introduced into a reaction vessel filled with 300 ml of deionized water thermostatically regulated to 37° C. The pH-value of the suspension was kept constant at pH 5 by means of an automatic burette through which lactic acid solution could be added. The quantity of 0.1 M lactic acid solution used for pH stabilization was recorded by a recorder. The consumption of lactic acid recorded after 2 hours corresponded to the solubility of the untreated hydroxyl apatite (Su).

2.2 Measurement

The measurement was carried out as in 2.1. 30 mg of the active substance to be tested were dissolved before addition of the hydroxyl apatite powder. The consumption of lactic acid recorded after 2 hours corresponded to the solubility of the treated apatite powder (St).

The reduction in apatite solubility by the active substance was calculated in accordance with the following equation:

$$ASR\ [\%] = \frac{(Su - St) \cdot 100}{Su}\ [\%]$$

The results of the measurements (ASR) are shown in Table I.

3. Determining the inhibition of crystal growth of hydroxyl apatite (CGI)

3.1 Blank test 400 ml of a 0.008 mol solution of $KH_2PO_4$ and 45 ml of a 0.012 mol solution of $CaCl_2$ were introduced into a reaction vessel. This solution was adjusted to pH 7.4 by titration with a 0.05 mol solution of KOH. After a pH value which remained stable for at least 30 minutes had been obtained, 100 mg of hydroxyl apatite powder (specific surface 60 $m^2/g$, Merck) were added. The pH-value of the suspension was kept constant at 7.4 by means of an automatic burette through which 0.05 M KOH solution could be added. The quantity of 0.05 M KOH solution used in stabilizing the pH value was recorded by a recorder. The consumption of KOH solution (Ku) recorded after 2 hours corresponded to the formation of hydroxyl apatite (growth of the crystals of the suspension).

3.2 Measurement

The measurement was carried out as in 3.1. 6 mg of the active substance to be tested were dissolved before adjustment of the pH-value.

The consumption of 0.05 M KOH solution (Kb) recorded after 2 hours corresponded to the formation of hydroxyl apatite (growth of the crystals in the suspension) under the effect of the active substance.

The inhibition of crystal growth by the active substance is calculated in accordance with the following equation:

$$CGI\ [\%] = \frac{(K_u - K_b) \cdot 100}{K_u}\ [\%]$$

The results of the measurements (CGI) are shown in Table I.

4. Determining the inhibition of phosphate ion exchange of hydroxyl apatite (PIE)

4.1 Blank test 1 g of hydroxyl apatite (specific surface 60 $m^2/g$, Merck) was introduced into a shaking vessel filled with 250 ml of a barbiturate buffer (pH 7) saturated with hydroxyl apatite, after which the suspension was shaken for 3 days at 20° C. for equilibrium adjustment. 1 ml of an $Na_2HPO_4$ solution in barbiturate buffer having a $^{32}P$-activity of 10 uCi 1 mCi $Na_2HPO_4$ (activity 200 Ci/mole) in 100 ml of barbiturate buffer) was then added. After 3 hours, a sample was taken, filtered through a membrane filter and the residual activity $A_{3h}$ determined. The inhibition of the phosphate ion exchange of the untreated hydroxyl apatite $$PIE\ [\%] = \frac{A_{3h}}{10\ \mu Ci} \cdot 100\ [\%]$$

amounted to 20%.

4.2 Pretreatment of the hydroxyl apatite with active substances 400 mg of the active substance dissolved in 10 ml of water were shaken for 24 hours with 3 g of hydroxyl apatite powder (specific surface 60 $m^2/g$, Merck) and 20 ml of a barbiturate buffer (pH 7) saturated with hydroxyl apatite. The hydroxyl apatite was then filtered off through a membrane filter and dried for 2 hours at 50° C.

4.3 Measurement 1 g of the pretreated hydroxyl apatite was analyzed in the same way as in 4.1. The inhibition of the phosphate ion exchange PIE [%] was calculated as follows from the loss of activity of the solution of the pretreated hydroxyl apatite:

$$PIE\ [\%] = \frac{A_{3h}}{10\ \mu Ci} \cdot 100\ [\%]$$

The results of the measurements (PIE) are shown in Table I.

TABLE I

| EX | Phosphoric acid Na-salt of glycerol + | CGI % inhibition of crystal growth | ASR % reduction of apatite solubility | PIE % inhibition of phosphate ion exchange |
|---|---|---|---|---|
| 1 | 1 mol E.O. | 53 | 39 | 69 |
| 2 | 2 mols E.O. | 44 | 29 | 65 |
| 3 | 3 mols E.O. | 46 | 25 | 65 |
| 4 | 7.3 mols E.O. | 44 | 14 | 55 |
| 5 | 10 mols E.O. | 20 | 16 | 60 |
| 6 | 1 mol P.O. | 25 | 29 | 71 |
| 7 | 2 mols P.O. | 34 | 32 | 69 |
| 8 | 3 mols P.O. | 18 | 18 | 61 |
| 9 | 6 mols P.O. | 21 | 25 | 58 |
| 10 | 10 mols P.O. | 21 | 10 | 51 |
| 11 | 13 mols P.O. | 11 | 6 | 56 |
| Comparison substances | | | | |
| | Glycerol phosphate (produced in accordance with 1.2) | 27 | 18 | 69 |
| | β-glycerol phosphate | 0 | 6 | 21 |
| | DL-α-glycerol phosphate | 0 | 1 | 24 |

5. Preparation Examples

5.1 Toothpaste

| | |
|---|---|
| Precipitated silica[1] | 18% by weight |
| Thickening silica (pyrogenic)[2] | 0.8% by weight |
| Glycerol + 1 mol E.O.-phosphate (according to Example 1) | 1.0% by weight |
| Sorbitol | 17.5% by weight |
| Glycerol | 17.5% by weight |
| Carboxymethyl cellulose[3] | 0.9% by weight |
| Sodium lauryl sulfate[4] | 2.0% by weight |
| Sodium fluoride | 0.22% by weight |
| Saccharin-sodium | 0.2% by weight |
| Flavoring oils | 1.0% by weight |
| Water, preservative | q.s. to 100% by weight |

5.2 Mouthwash

| | |
|---|---|
| Ethyl alcohol (96% by vol.) | 10% by weight |
| Polyoxyethylene sorbitan monolaurate[5] | 0.4% by weight |
| Flavoring oil | 0.3% by weight |
| Sorbitol (70% aqueous solution) | 8.0% by weight |
| p-hydroxybenzoic acid methyl ester | 0.16% by weight |
| Glycerol + 1 mol E.O. phosphate (according to Example 1) | 0.1% by weight |
| Saccharin-sodium | 0.1% by weight |
| Water, dyes | q.s. to 100% by weight |

[1]"Sident 12DS, a product of Degussa, Fed. Rep. of Germany
[2]"Aerosil" 200, a product of Degussa Corp. U.S.A.*
[3]"Relatin" 100 S8 a product of Henkel KgaA, Fed. Rep. of Germany
[4]"Texapon" K1296, a product of Henkel Corp. U.S.A./Canada*
[5]"Tween" 20, a product of ICI Americas, Inc., U.S.A.*
*(The foregoing trademarked products were actually obtained from related companies in the Federal Republic of Germany.)

We claim:

1. A process for inhibiting dental caries comprising contacting the surface of a tooth with an oral and dental hygiene preparation containing a $C_2$–$C_4$-alkoxylated trihydric to hexahydric $C_3$–$C_{12}$-aliphatic polyol wherein at least one hydroxyl moiety is esterified with phosphoric acid, or a physiologically compatible water soluble salt thereof in a non-toxic amount sufficient to inhibit dental caries in said tooth.

2. The process of claim 1 wherein in said preparation the polyol is at least one of glycerol, erythritol, trimethylol propane, pentaerythritol, arabitol, xylitol, sorbitol, manitol, diglycerol, triglycerol, dipentaerythritol, or trimethylol ethane.

3. The process of claim 1 wherein in said preparation the polyol is at least one of glycerol, erythritol, trimethylol propane, or pentaerythritol.

4. The process of claim 1 wherein in said preparation the polyol is glycerol.

5. The process of claim 1 wherein in said preparation the aliphatic polyol is alkoxylated with 1 to 15 mols of $C_2$–$C_4$ alkylene oxide.

6. The process of claim 3 wherein in said preparation the aliphatic polyol is alkoxylated with 1 to 15 mols of $C_2$–$C_4$ alkylene oxide.

7. The process of claim 1 wherein in said preparation the aliphatic polyol is alkoxylated with 1 to 10 mols of $C_2$–$C_4$ alkylene oxide.

8. The process of claim 3 wherein in said preparation the aliphatic polyol is alkoxylated with 1 to 10 mols of $C_2$–$C_4$ alkylene oxide.

9. The process of claim 1 wherein in said preparation the aliphatic polyol is alkoxylated with 1 to 7 mols of $C_2$–$C_4$ alkylene oxide.

10. The process of claim 4 wherein in said preparation the aliphatic polyol is alkoxylated with 1 to 7 mols of $C_2$–$C_4$ alkylene oxide.

11. The process of claim 1 wherein in said preparation the aliphatic polyol is alkoxylated with ethylene oxide, propylene oxide, or both.

12. The process of claim 6 wherein in said preparation the aliphatic polyol is alkoxylated with ethylene oxide, propylene oxide, or both.

13. The process of claim 8 wherein in said preparation the aliphatic polyol is alkoxylated with ethylene oxide, propylene oxide, or both.

14. The process of claim 10 wherein in said preparation the aliphatic polyol is alkoxylated with ethylene oxide, propylene oxide, or both.

15. The process of claim 1 wherein in said preparation the soluble salt is present and is at least one of sodium, potassium, ammonium, monoethanolammonium, diethanolammonium, triethanolammonium, calcium, or magnesium.

16. The process of claim 1 wherein in said preparation the salt is present and is sodium or potassium.

17. The process of claim 6 wherein in said preparation the salt is present and is sodium or potassium.

18. The process of claim 8 wherein in said preparation the salt is present and is sodium or potassium.

19. The process of claim 10 wherein in said preparation the salt is present and is sodium or potassium.

20. The process of claim 14 wherein in said preparation the salt is present and is sodium or potassium.

21. The process of claim 1 wherein in said preparation the phosphoric acid ester is present in 0.05 to 5.0% by weight based upon the weight of the entire preparation.

22. The process of claim 1 wherein said preparation is in the form of a paste toothpaste containing 0.1 to 2.0% by weight of said ester and further including an abrasive polish which at least predominantly consists essentially of finely particulate xerogel silica, hydrogel silica, precipitated silica, aluminum oxide trihydrate, finely particulate aluminum oxide, or any mixture thereof.

23. The process of claim 20 wherein said preparation is in the form of a paste toothpaste containing 0.1 to 2.0% by weight of said ester and further including an abrasive polish which at least predominantly consists essentially of finely particulate xerogel silica, hydrogel silica, precipitated silica, aluminum oxide trihydrate, finely particulate aluminum oxide, or any mixture thereof.

24. The process of claim 1 wherein said preparation is in the form of a mouthwash containing 0.05 to 1% by weight of said ester and also containing water, alcohol, or a mixture thereof.

25. The process of claim 20 wherein said preparation is in the form of a mouthwash containing 0.05 to 1% by weight of said ester and further including water, alcohol, or a mixture thereof.

26. The process of claim 1 wherein in said preparation substantially all hydroxyl moieties of said polyol are esterified.

27. The process of claim 6 wherein in said preparation substantially all hydroxyl moieties of said polyol are esterified.

28. The process of claim 8 wherein in said preparation substantially all hydroxyl moieties of said polyol are esterified.

29. The process of claim 10 wherein in said preparation substantially all hydroxyl moieties of said polyol are esterified.

30. The process of claim 14 wherein in said preparation substantially all hydroxyl moieties of said polyol are esterified.

* * * * *